United States Patent
Amano

(10) Patent No.: US 12,149,804 B2
(45) Date of Patent: Nov. 19, 2024

(54) CAMERA HEAD FOR ENDOSCOPE

(71) Applicant: Sony Olympus Medical Solutions Inc., Tokyo (JP)

(72) Inventor: Kohtaro Amano, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 391 days.

(21) Appl. No.: 17/588,339

(22) Filed: Jan. 30, 2022

(65) Prior Publication Data
US 2022/0159147 A1    May 19, 2022

Related U.S. Application Data

(63) Continuation of application No. 15/897,182, filed on Feb. 15, 2018, now abandoned.

(30) Foreign Application Priority Data

Mar. 10, 2017 (JP) .................. 2017-046647

(51) Int. Cl.
| | |
|---|---|
| H04N 23/51 | (2023.01) |
| A61B 1/04 | (2006.01) |
| A61B 1/05 | (2006.01) |
| G03B 17/08 | (2021.01) |
| G03B 17/48 | (2021.01) |
| H04N 23/50 | (2023.01) |
| A61B 1/00 | (2006.01) |
| A61B 1/07 | (2006.01) |

(52) U.S. Cl.
CPC ............. *H04N 23/51* (2023.01); *A61B 1/042* (2013.01); *A61B 1/053* (2013.01); *G03B 17/08* (2013.01); *G03B 17/48* (2013.01); *A61B 1/00114* (2013.01); *A61B 1/07* (2013.01); *H04N 23/555* (2023.01)

(58) Field of Classification Search
None
See application file for complete search history.

(56) References Cited

U.S. PATENT DOCUMENTS

| | | |
|---|---|---|
| 4,307,904 A | 12/1981 | Daus |
| 4,854,302 A | 8/1989 | Allred, III |
| 5,311,859 A | 5/1994 | Monroe et al. |
| 5,609,561 A | 3/1997 | Uehara et al. |
| 5,783,873 A | 7/1998 | Dohan et al. |
| 6,500,169 B1 | 12/2002 | Deng |
| 6,805,665 B1 | 10/2004 | Tatsuno et al. |
| 7,004,491 B1 | 2/2006 | Allsop et al. |
| 7,608,039 B1 | 10/2009 | Todd |

(Continued)

FOREIGN PATENT DOCUMENTS

| | | |
|---|---|---|
| JP | H05-337078 A | 12/1993 |
| JP | 2008-104851 A | 5/2008 |

(Continued)

OTHER PUBLICATIONS

Office Action issued on Nov. 17, 2020, in corresponding Japanese patent Application No. 2017-046647, 6 pages.

*Primary Examiner* — John P Leubecker
(74) *Attorney, Agent, or Firm* — XSENSUS LLP

(57) ABSTRACT

A camera head for an endoscope includes a casing that forms exterior, and an imaging unit that is housed in the casing and images a subject image. The casing includes a metal exterior unit that forms at least a part of the exterior and is formed by hydroforming.

27 Claims, 9 Drawing Sheets

(56) References Cited

U.S. PATENT DOCUMENTS

| | | |
|---|---|---|
| 8,545,396 B2 | 10/2013 | Cover et al. |
| 8,972,714 B2 | 3/2015 | Talbert et al. |
| 2001/0016679 A1 | 8/2001 | Futatsugi et al. |
| 2004/0263616 A1 | 12/2004 | Yamaguchi |
| 2005/0267329 A1 | 12/2005 | Konstorum et al. |
| 2006/0173242 A1 | 8/2006 | Navok et al. |
| 2007/0004965 A1 | 1/2007 | Ogino et al. |
| 2008/0086033 A1 | 4/2008 | Mihalca |
| 2008/0311348 A1 | 12/2008 | Miyachi |
| 2015/0062153 A1 | 3/2015 | Mihalca et al. |
| 2016/0338580 A1 | 11/2016 | Amano |
| 2017/0168287 A1 | 6/2017 | Lietzau |
| 2018/0263471 A1 | 9/2018 | Ohno |
| 2018/0348502 A1 | 12/2018 | Tanahashi |
| 2019/0167074 A1 | 6/2019 | Malinskiy et al. |

FOREIGN PATENT DOCUMENTS

| | | |
|---|---|---|
| JP | 2008-522790 A | 7/2008 |
| JP | 2010-509990 A | 4/2010 |
| JP | 2012-245045 A | 12/2012 |
| JP | 2013-526323 A | 6/2013 |

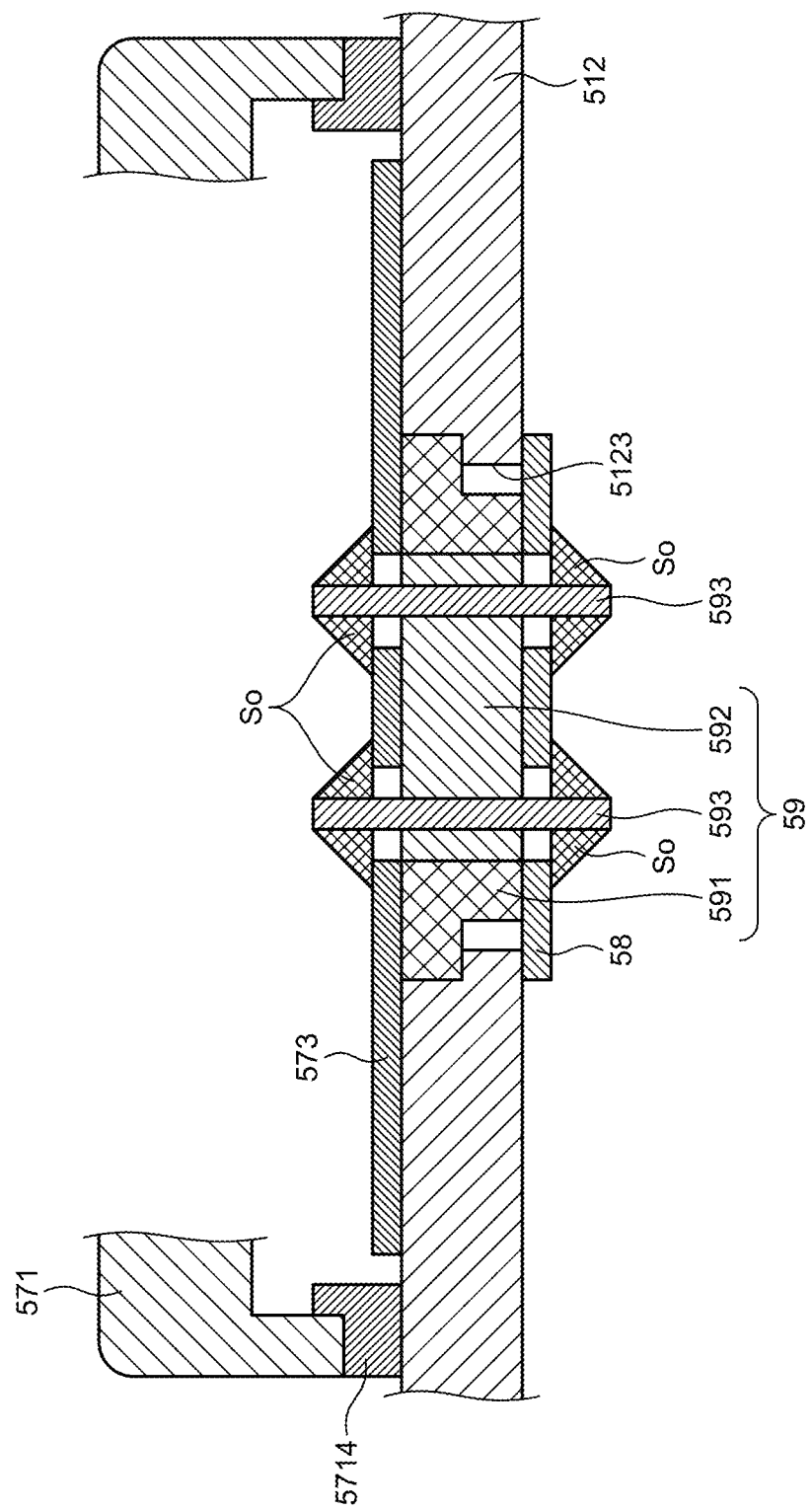

CAMERA HEAD FOR ENDOSCOPE

CROSS-REFERENCE TO RELATED APPLICATIONS

This application is a continuation of U.S. application Ser. No. 15/897,182, filed Feb. 15, 2018, which claims priority to Japanese Application No. 2017-046647, filed Mar. 10, 2017, the entire contents of each are incorporated herein by reference.

BACKGROUND

The present disclosure relates to a camera head for an endoscope.

In the related art, there has been known an endoscopic device that images the inside of a subject (the inside of a living body) such as a human being by using an imaging element and observes the inside of the living body (for example, Japanese Laid-open Patent Publication No. 2012-245045).

An endoscopic device (endoscopic system) disclosed in Japanese Laid-open Patent Publication No. 2012-245045 includes a head-separated endoscopic device. Specifically, the endoscopic device includes an insertion unit (endoscope) that is inserted into a living body, a camera head for an endoscope (camera head) that includes an imaging element imaging a subject image condensed by the insertion unit, a controller (image processor) that processes an image signal output from the imaging element, and a cable that electrically connects between the imaging element and the controller.

In the camera head for an endoscope, the imaging element is arranged in a casing (airtight casing) the inside of which is held airtight so that the imaging element may be protected from a chemical solution used at the time of sterilization processing in wiping and liquid immersion, and from high temperature and high pressure steam in autoclave treatment (high temperature and high pressure steam sterilization processing).

SUMMARY

A casing of a camera head for an endoscope is generally formed of a metal material, and is formed by cutting processing and casting such as lost wax.

However, when a casing is formed by cutting processing and casting, it is difficult to form the casing to be thin. In other words, it is difficult to reduce size and weight of a camera head for an endoscope.

A camera head for an endoscope according to one aspect of the present disclosure includes: a casing that forms exterior; and an imaging unit that is housed in the casing and images a subject image, wherein the casing includes a metal exterior unit that forms at least a part of the exterior and is formed by hydroforming.

A camera head for an endoscope according to another aspect of the present disclosure includes: a casing that forms exterior; and an imaging unit that is housed in the casing and images a subject image, wherein the casing includes a metal exterior unit that forms at least a part of the exterior and is formed by deep drawing processing.

BRIEF DESCRIPTION OF THE DRAWINGS

FIG. 5 is a sectional view illustrating a connection configuration of an operation board and an internal board;

DETAILED DESCRIPTION

Figure 1:
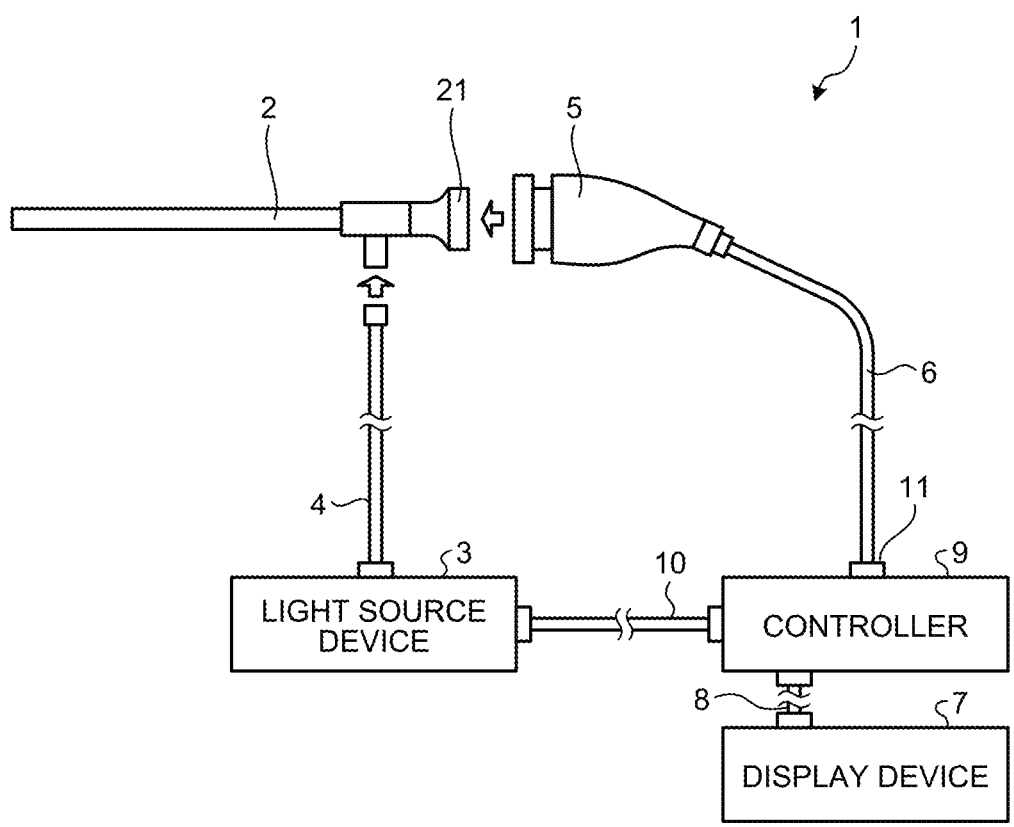
FIG. 1 is a view illustrating a schematic configuration of an endoscopic device according to an embodiment.

An embodiment for implementing the present disclosure (hereinafter, an embodiment) will now be described with reference to the accompanying drawings. It should be noted that the embodiment described below is not intended to limit the present disclosure. In the description of the drawings, like reference numerals indicate like components.

Schematic Configuration of Endoscopic Device

FIG. 1 is a view illustrating a schematic configuration of an endoscopic device 1 according to an embodiment.

The endoscopic device 1 is used in a medical field, and is a device for observing the inside of a living body. As illustrated in FIG. 1, this endoscopic device 1 includes an insertion unit 2, a light source device 3, a light guide 4, a camera head for an endoscope 5, a first transmission cable 6, a display device 7, a second transmission cable 8, a controller 9, and a third transmission cable 10.

The insertion unit 2 includes a rigid endoscope. In other words, the insertion unit 2 is rigid or a part of which is flexible, the insertion unit 2 has a slender shape, and is inserted into a living body. In the insertion unit 2, there is provided an optical system that includes one or a plurality of lenses and condenses a subject image.

The light source device 3 is connected to one end of the light guide 4, and supplies light for illuminating the inside of a living body to the one end of the light guide 4 under control of the controller 9.

One end of the light guide 4 is attachably and detachably connected to the light source device 3, and the other end is attachably and detachably connected to the insertion unit 2. The light guide 4 transmits the light supplied from the light source device 3 from the one end to the other end, and supplies the light to the insertion unit 2. The light supplied to the insertion unit 2 is emitted from the tip end of the insertion unit 2 and is emitted to the inside of a living body. The light (subject image) that is emitted to the inside of a living body and is reflected in the living body is condensed by the optical system in the insertion unit 2.

The camera head for an endoscope 5 is attachably and detachably connected to a base end of the insertion unit 2 (eyepiece unit 21 (FIG. 1)). The camera head for an endoscope 5 images a subject image condensed by the insertion unit 2 under control of the controller 9, and outputs an image signal (RAW signal) generated by the imaging. The image signal is, for example, an image signal of 4K or more.

A detailed configuration of the camera head for an endoscope 5 will be described later.

Figure 2:
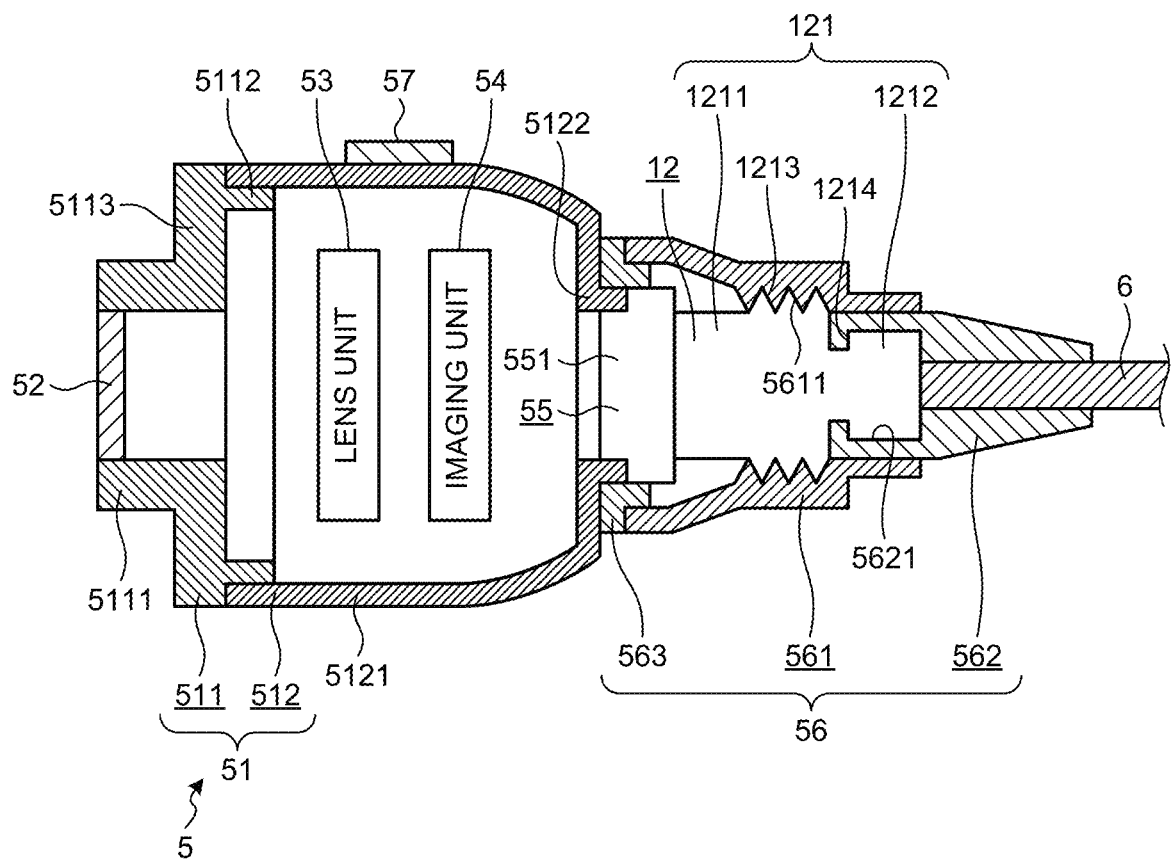
FIG. 2 is a sectional view illustrating a schematic configuration of a camera head for an endoscope.

One end of the first transmission cable 6 is attachably and detachably connected to the controller 9 through a connector 11 (FIG. 1), and the other end thereof is attachably and detachably connected to the camera head for an endoscope 5 through a connector 12 (FIG. 2). The first transmission cable 6 transmits an image signal and the like output by the camera head for an endoscope 5 to the controller 9, and transmits a control signal, a synchronization signal, a clock, power, and the like output from the controller 9 to the camera head for an endoscope 5.

As for transmission of an image signal and the like from the camera head for an endoscope 5 to the controller 9 through the first transmission cable 6, the image signal and the like may be transmitted as an optical signal or may be transmitted as an electric signal. The same applies to transmission of a control signal, a synchronization signal, and a clock from the controller 9 to the camera head for an endoscope 5 through the first transmission cable 6.

The display device 7 includes a display with liquid crystal or electro luminescence and the like, and displays an image based on a video signal from the controller 9 under control of the controller 9.

One end of the second transmission cable 8 is attachably and detachably connected to the display device 7, and the other end thereof is attachably and detachably connected to the controller 9. The second transmission cable 8 transmits a video signal processed by the controller 9 to the display device 7.

The controller 9 includes a central processing unit (CPU) and the like, and integrally controls the operation of the light source device 3, the camera head for an endoscope 5, and the display device 7.

For example, the controller 9 performs various kinds of processing on an image signal acquired from the camera head for an endoscope 5 through the first transmission cable 6 so as to generate a video signal, and outputs the video signal to the display device 7 through the second transmission cable 8. The display device 7 displays an image based on the video signal. The controller 9 outputs a control signal and the like to the camera head for an endoscope 5 and the light source device 3 through the first transmission cable 6 and the third transmission cable 10, respectively.

One end of the third transmission cable 10 is attachably and detachably connected to the light source device 3, and the other end thereof is attachably and detachably connected to the controller 9. The third transmission cable 10 transmits a control signal from the controller 9 to the light source device 3.

Configuration of Camera Head for Endoscope

Figure 3:
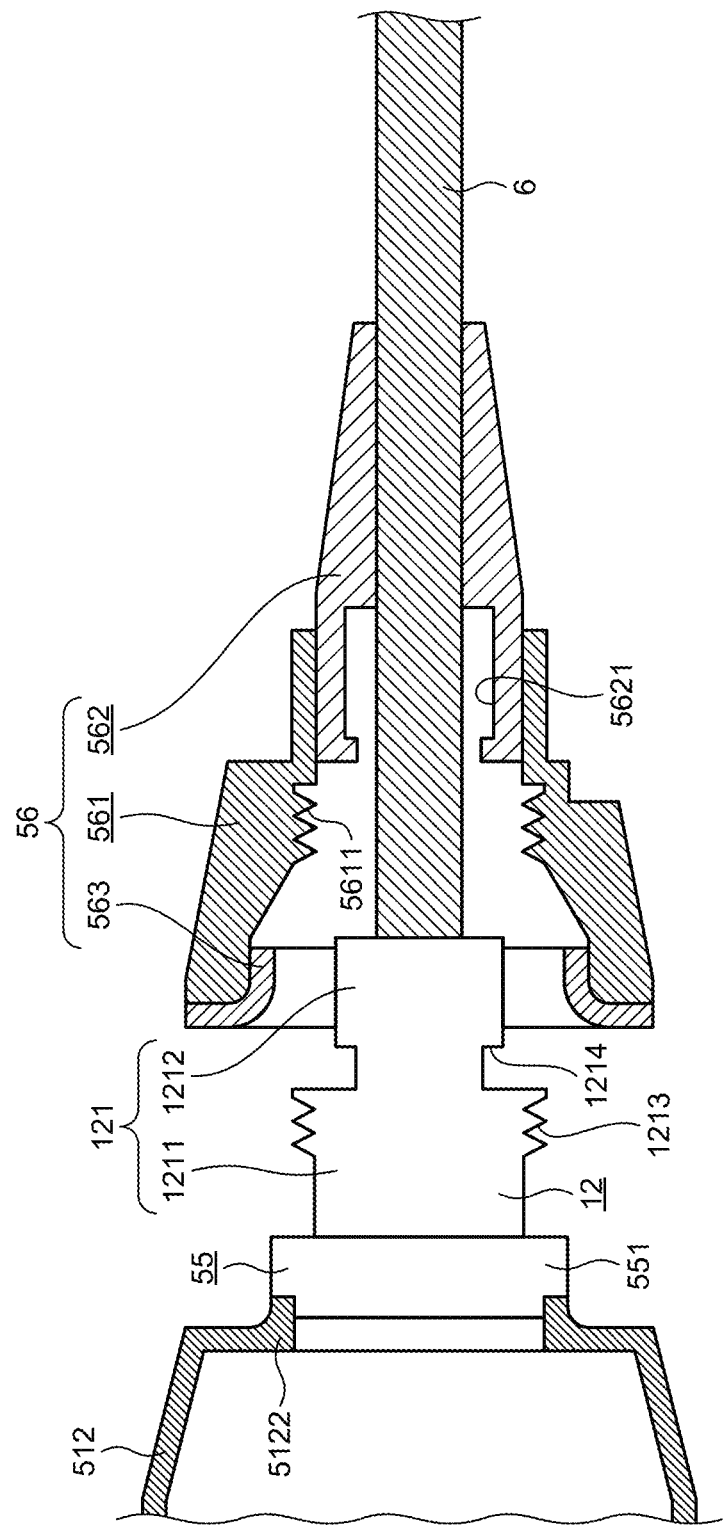
FIG. 3 is a view where a part in FIG. 2 is enlarged and is a sectional view illustrating a state where a base end sealing member is removed from a connector.

The following describes the configuration of the camera head for an endoscope 5. FIG. 2 is a sectional view illustrating a schematic configuration of the camera head for an endoscope 5. FIG. 3 is a view where a part in FIG. 2 is enlarged and is a sectional view illustrating a state where a base end sealing member 56 is removed from the connector 12.

A "tip end", which will be described later, indicates an end part (left end part in FIG. 2) of a side to which a base end of the insertion unit 2 (eyepiece unit 21) is connected. A "base end" indicates an end part (right end part in FIG. 2) of a side to which the first transmission cable 6 is connected.

As illustrated in FIG. 2 or 3, the camera head for an endoscope 5 includes a casing 51, an optical element 52 (FIG. 2), a lens unit 53 (FIG. 2), an imaging unit 54 (FIG. 2), a hermetic connector 55, the base end sealing member 56, and an operating unit 57.

The casing 51 forms exterior, and houses therein the lens unit 53 and the imaging unit 54. In the embodiment, the casing 51 includes two casings that are a front casing 511 and a rear casing 512 as illustrated in FIG. 2.

The front casing 511 is a member that holds the optical element 52 and fixes the optical element 52 to the rear casing 512, and is formed of any metal material out of aluminum, an aluminum alloy, stainless steel, titanium, and a titanium alloy. The front casing 511 includes first and second tubular parts 5111 and 5112, and a connection part 5113 as illustrated in FIG. 2.

The first tubular part 5111 is formed in a tubular shape (for example, a cylindrical shape), and is disposed on the tip end side. The first tubular part 5111 holds the optical element 52 on the inner periphery.

The second tubular part 5112 is formed in a tubular shape (for example, a cylindrical shape) having an internal size larger than an external size of the first tubular part 5111, and is disposed on the base end side.

The connection part 5113 is formed in a circular shape (for example, an annular shape), and is disposed between the first and the second tubular parts 5111 and 5112.

The first and the second tubular parts 5111 and 5112, and the connection part 5113 are integrally formed so that their center axes may coincide with each other.

The front casing 511 described above is formed by, for example, cutting processing.

The rear casing 512 forms a part of the exterior, and is formed by hydroforming. The rear casing 512 is formed of any metal material out of aluminum, an aluminum alloy, stainless steel, titanium, and a titanium alloy. In other words, the rear casing 512 corresponds to an exterior unit according to the present disclosure. A method for manufacturing the rear casing 512 (hydroforming) will be described later.

As illustrated in FIG. 2, in this rear casing 512, a tip end part 5121 and a base end part 5122 each have a tubular shape (for example, a cylindrical shape) including an aperture. More specifically, the rear casing 512 extends in substantially the same internal size from the tip end part 5121 to the base end part 5122 side, and has the internal size narrowed at the base end part 5122.

The front casing 511 and the rear casing 512 are fixed to each other by welding while the second tubular part 5112 is engaged with the inside of the tip end part 5121. In other words, a part between the front casing 511 and the rear casing 512 is air-tightly sealed. The front casing 511 corresponds to an adjacent exterior unit according to the present disclosure.

The optical element 52 is fixed to the inside of the first tubular part 5111 by brazing, and air-tightly seals an aperture on the tip end side of the casing 51. This optical element 52 is formed in a flat sheet shape, and is formed of, for example, sapphire glass.

The lens unit 53 forms a subject image that is condensed at the insertion unit 2, on an imaging surface of the imaging unit 54 with the optical element 52 interposed between the insertion unit 2 and the lens unit 53. Depending on operation to the operating unit 57 operated by a user such as a doctor, for example, a driving motor (not illustrated) housed in the casing 51 causes the lens unit 53 to move in an optical axis direction so as to make it possible to adjust a focal length and focus.

The imaging unit 54 images the inside of a living body under control of the controller 9. This imaging unit 54 includes a sensor chip in which an imaging element (not illustrated), such as a charge coupled device (CCD) or a complementary metal oxide semiconductor (CMOS), that receives a subject image condensed at the insertion unit 2 and formed by the lens unit 53 through the optical element 52 and converts the subject image to an electric signal, a signal processor (not illustrated) performing signal processing (analog/digital (A/D) conversion and the like) on the electric signal from the imaging element and outputting an image signal, and the like are integrally formed. The imaging unit 54 outputs an image signal (digital signal) after A/D conversion. The signal processor described above does not need to be integrally formed with the imaging element and may be separately formed.

As illustrated in FIG. 2 or 3, the hermetic connector 55 includes a tubular (for example, a cylindrical) outer shell 551, a sheet body (not illustrated) that closes the inside of the outer shell 551, and a plurality of conductive pins (not illustrated) that penetrate through the front and back of the sheet body, the conductive pins being attached to the sheet body while being isolated from each other and electrically connected to the imaging unit 54. The outer shell 551 is formed of any metal material out of aluminum, an aluminum alloy, stainless steel, titanium, and a titanium alloy. In the hermetic connector 55, the outer shell 551 is fixed to the base end part 5122 by welding and air-tightly seals an aperture on the base end side of the casing 51.

It is preferable that the front casing 511, the rear casing 512, and the hermetic connector 55 (outer shell 551) described above be formed of the same material because they are fixed to each other by welding.

The connector 12 is attachably and detachably connected to the hermetic connector 55.

As illustrated in FIG. 2 or 3, the connector 12 includes a tubular (for example, a cylindrical) outer shell 121, an insulator (not illustrated) that closes the inside of the outer shell 121, and a plurality of contacts (not illustrated) that are provided to the insulator. The contacts have, at the time of attaching the connector 12 to the hermetic connector 55, the conductive pins of the hermetic connector 55 inserted therein and are electrically connected to the conductive pins, and are electrically connected to the first transmission cable 6.

In other words, an image signal (RAW signal (digital signal)) output from the imaging unit 54 is output to the first transmission cable 6 through the hermetic connector 55 and the connector 12. A control signal and the like output from the controller 9 are output to electronic components (including the imaging unit 54) in the casing 51 through the first transmission cable 6, the connector 12, and the hermetic connector 55.

At the time of attaching the connector 12 to the hermetic connector 55, an unillustrated fixture prevents the outer shells 551 and 121 from being removed from each other.

The base end sealing member 56 is a member that water-tightly seals a part among the first transmission cable 6, the connector 12, and the hermetic connector 55.

Before the configuration of the base end sealing member 56 is described, a shape of the outer shell 121 of the connector 12 is described.

As illustrated in FIG. 2 or 3, in the outer shell 121, an outer shell body 1211 and a locking swelling unit 1212 are integrally formed.

The outer shell body 1211 has a tubular shape (for example, a cylindrical shape). On the outer surface of the outer shell body 1211, a screw groove 1213 is formed.

The locking swelling unit 1212 has a tubular shape (for example, a cylindrical shape), and is integrally formed with a base end of the outer shell body 1211 so that the center axis of the locking swelling unit 1212 may coincide with that of the outer shell body 1211. The locking swelling unit 1212 has an external size smaller than that of the outer shell body 1211. In addition, the locking swelling unit 1212 has a larger external size on the base end side than that of the tip end side, and includes a step 1214.

As illustrated in FIG. 2 or 3, the base end sealing member 56 includes a cable bushing 561, a cable protective boot 562, and a seal unit 563.

The cable bushing 561 has a tubular shape (for example, a cylindrical shape) having an external size and an internal size narrowed from the tip end side to the base end side. The cable bushing 561 is formed of super engineering plastic such as polyphenylene sulfide (PPS), polyphenylsulfone (PPSU), polyetheretherketone (PEEK), and polyethersulfone (PES), or any metal material out of stainless steel, titanium, and a titanium alloy. On the inner surface of the cable bushing 561, a screw groove 5611 corresponding to the screw groove 1213 is formed. In other words, the cable bushing 561 is fixed to the connector 12 by screwing the screw groove 5611 to the screw groove 1213.

The cable protective boot 562 has a tubular shape (for example, a cylindrical shape), and is provided between an inner surface on the base end side of the cable bushing 561 and an outer surface of the first transmission cable 6. This cable protective boot 562 is formed of silicone rubber or Teflon (registered trademark) rubber or the like. An internal size of the cable protective boot 562 is set (interference-fitted) to be smaller than an external size of the first transmission cable 6. In addition, on the inner surface on the tip end side of the cable protective boot 562, a locking recessed part 5621 with which the locking swelling unit 1212 is engaged and that is locked with the step 1214 is formed. In other words, the cable protective boot 562 is prevented from being separated from the connector 12 by being locked to the step 1214.

The seal unit 563 has substantially a cylindrical shape, and is provided between an inner surface on the tip end side of the cable bushing 561 and outer surfaces of the base end part 5122 and the hermetic connector 55. The seal unit 563 is formed of silicone rubber or Teflon rubber and the like.

The cable bushing 561, the cable protective boot 562, and the seal unit 563 described above are formed by integral molding.

Examples of the integral molding may include insert molding where the previously formed cable bushing 561 is held in a metal mold and a rubber part (the cable protective boot 562 and the seal unit 563) is formed and multi-color molding where the plastic cable bushing 561 is formed, and a rubber part (the cable protective boot 562 and the seal unit 563) is formed while the cable bushing 561 is held in a metal mold.

In the embodiment, the cable bushing 561, the cable protective boot 562, and the seal unit 563 are integrally formed, but only the cable bushing 561 and the cable protective boot 562 may be integrally formed or only the cable bushing 561 and the seal unit 563 may be integrally formed.

Figure 4:
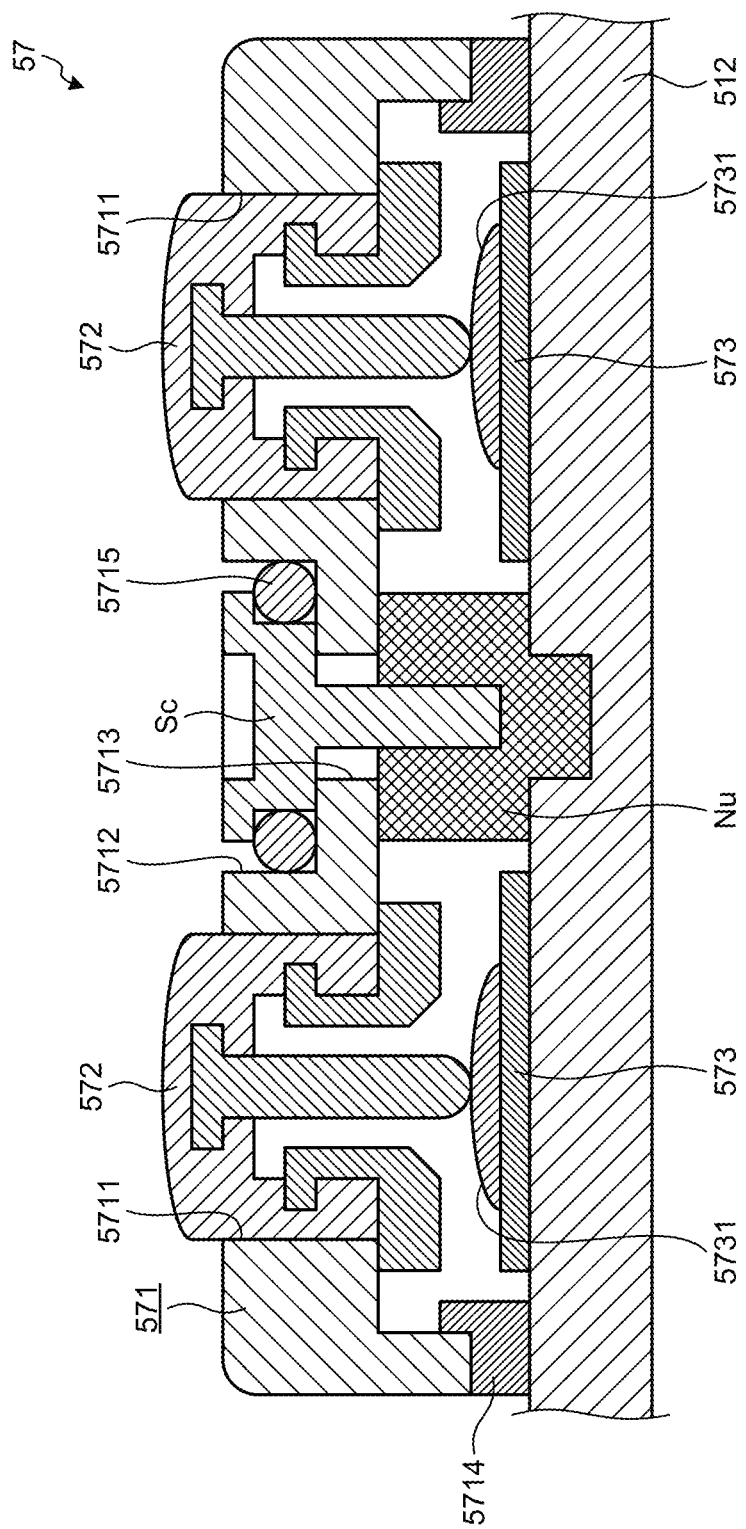
FIG. 4 is a sectional view illustrating a schematic configuration of an operating unit.

FIG. 4 is a sectional view illustrating a schematic configuration of the operating unit 57.

As illustrated in FIG. 4, the operating unit 57 is attached to an outer surface of the rear casing 512 using a nut Nu fixed to the outer surface of the rear casing 512 by laser welding and a screw Sc fastened to the nut Nu. In other words, the operating unit 57 corresponds to an outer surface arrangement member according to the present disclosure. The nut Nu corresponds to a base according to the present disclosure. The operating unit 57 receives user operation operated by a user such as a doctor. As illustrated in FIG. 4, this operating unit 57 includes a button frame 571, a plurality of operation buttons 572, and an operation board 573.

The button frame 571 is formed in a container shape having the lower side open in FIG. 4. On the bottom surface of this button frame 571 (in FIG. 4, a surface on an upper side), a plurality of apertures 5711 that communicate the inside and outside of the button frame 571 and each have the operation buttons 572 arranged thereon are formed. On the bottom surface of the button frame 571, in FIG. 4, a recessed part 5712 that recesses a lower side is also formed. In addition, on the bottom surface of the recessed part 5712, an insertion hole 5713 in which the screw Sc is inserted is formed. The button frame 571 is attached to the outer surface of the rear casing 512 with the screw Sc by screwing the screw Sc to the nut Nu through the insertion hole 5713. As illustrated in FIG. 4, seal units 5714 and 5715 such as an O-ring water-tightly seal a part between the button frame 571 and the outer surface of the rear casing 512 and a part between the insertion hole 5713 and the screw Sc.

The operation buttons 572 are parts pressed down by a user such as a doctor, and are disposed movably in the vertical direction in the apertures 5711 in FIG. 4.

As illustrated in FIG. 4, the operation board 573 is attached to the outer surface of the rear casing 512 and is covered with the button frame 571. This operation board 573 has a plurality of tact switches 5731 implemented thereon corresponding to the operation buttons 572, and receives operation depending on pressing of the operation buttons 572 by a user such as a doctor. The operation board 573 outputs an operation signal depending on the operation to an internal board 58 (see FIG. 5) disposed in the rear casing 512.

FIG. 5 is a sectional view illustrating a connection configuration of the operation board 573 and the internal board 58.

As illustrated in FIG. 5, the operation board 573 and the internal board 58 are electrically connected to each other through a hermetic connector 59.

As illustrated in FIG. 5, this hermetic connector 59 includes a tubular (for example, a cylindrical) outer shell 591, an insulating sheet body 592 that is formed of glass and the like and closes the inside of the outer shell 591, and a plurality of conductive pins 593 that penetrate through the front and back of the sheet body 592. The hermetic connector 59 is fixed to the rear casing 512 by connecting an inner surface of a through-hole 5123 formed on the rear casing 512 and an outer surface of the outer shell 591 using laser-welding while engaged with the through-hole 5123. In other words, the through-hole 5123 is air-tightly sealed by the hermetic connector 59.

The operation board 573 is electrically connected to the conductive pins 593 by soldering So. Similarly, the internal board 58 is electrically connected to the conductive pins 593 by soldering So. In other words, the operation board 573 and the internal board 58 are electrically connected to each other through the conductive pins 593.

The number of the conductive pins 593 may be one.

Method for Manufacturing Rear Casing

The following describes a method for manufacturing the rear casing 512 (hydroforming).

FIGS. 6A to 6E are views illustrating the method for manufacturing the rear casing 512.

Hereinafter, for convenience, a member to be formed by hydroforming is defined as a target member Ta that is different from the rear casing 512.

The target member Ta is a tubular member on which rolling and extrusion processing is performed.

Figure 6A:
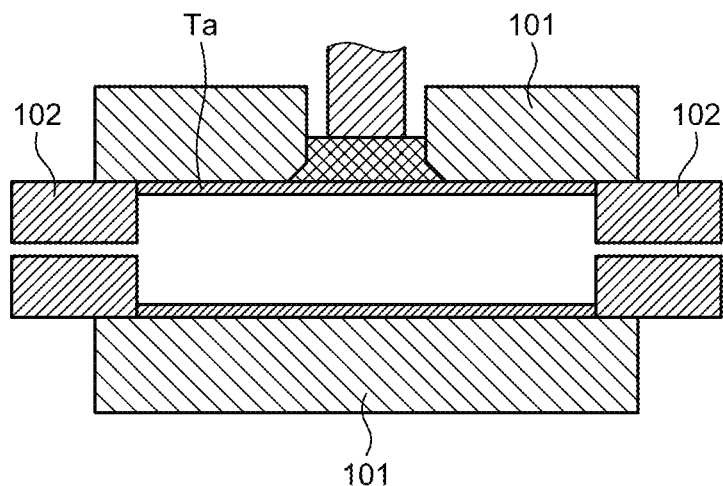
FIG. 6A is a view illustrating a method for manufacturing a rear casing.

As illustrated in FIG. 6A, the target member Ta is placed in a pair of metal molds 101 that have an internal shape following an external shape of a member to be formed.

Figure 6B:
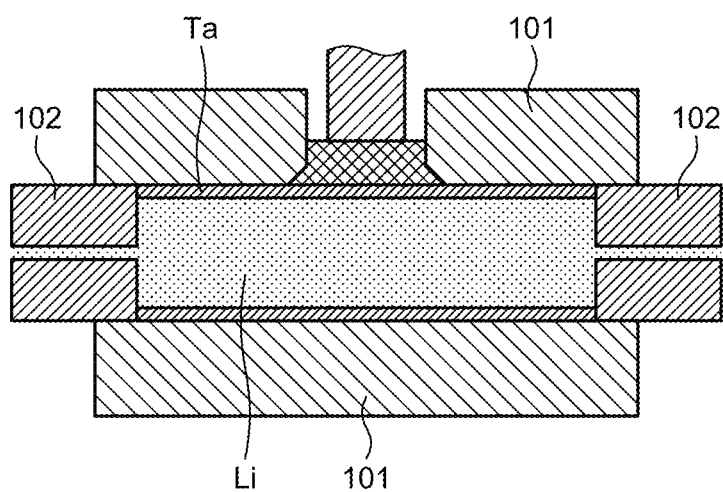
FIG. 6B is a view illustrating a method for manufacturing the rear casing.

Subsequently, as illustrated in FIG. 6B, while left-right pistons 102 sandwich the target member Ta and seal apertures at both ends of the target member Ta, liquid Li is injected into the target member Ta.

Figure 6C:
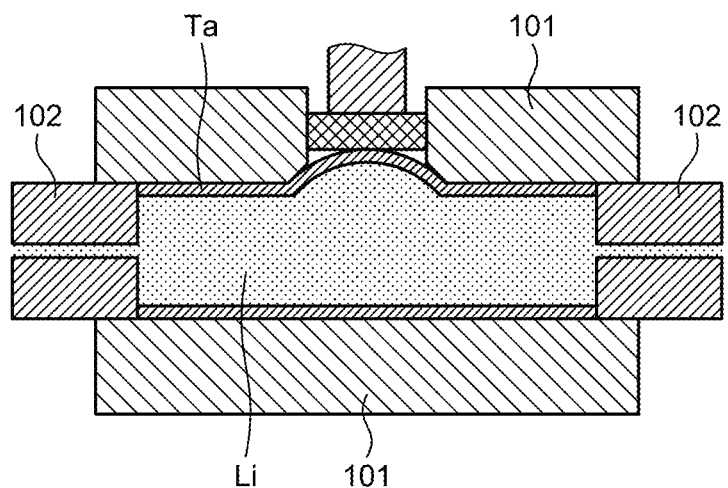
FIG. 6C is a view illustrating a method for manufacturing the rear casing.
Figure 6D:
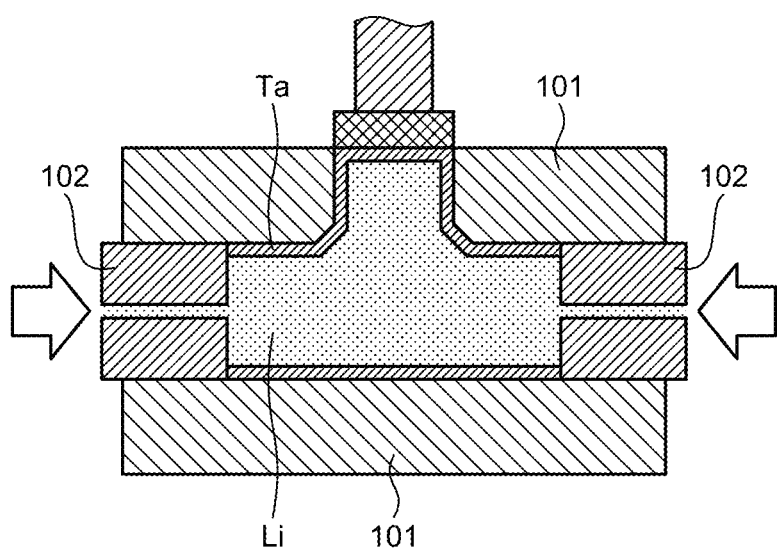
FIG. 6D is a view illustrating a method for manufacturing the rear casing.

Subsequently, as illustrated in FIGS. 6C and 6D, pressure of the liquid Li is increased so as to expand the target member Ta into a desired shape. At this time, as illustrated in FIG. 6D, the left-right pistons 102 compress the target member Ta in the axial direction so as to supply a material to an expanded part and prevent a decrease in sheet thickness.

Figure 6E:
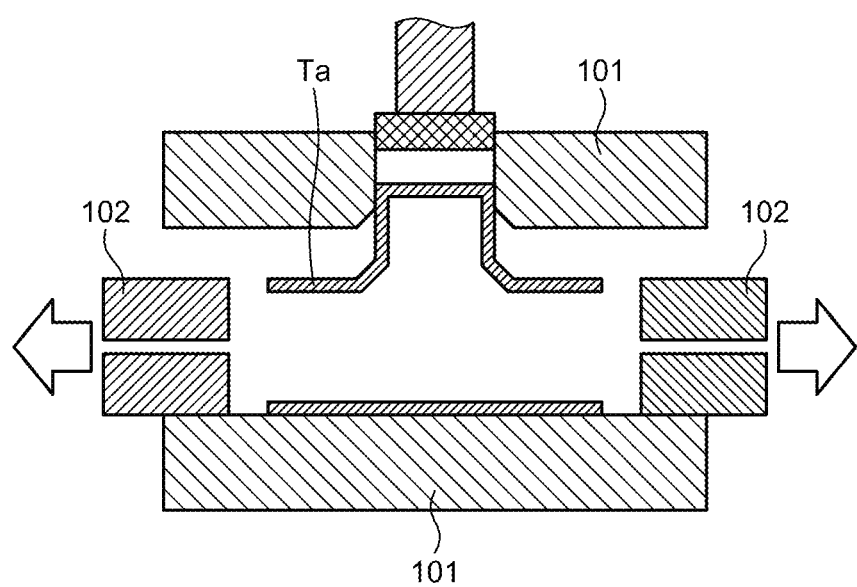
FIG. 6E is a view illustrating a method for manufacturing the rear casing.

Subsequently, as illustrated in FIG. 6E, the pair of metal molds 101 and the left-right pistons 102 are separated from each other so as to complete the forming of the target member Ta.

According to the embodiment described above, the following effect is exhibited.

In the camera head for an endoscope 5 according to the embodiment, the rear casing 512 is formed by hydroforming. In other words, the rear casing 512 may be formed to be thin by using hydroforming. Thus, the camera head for an endoscope 5 according to the embodiment may achieve reduction of size and weight of an endoscopic device.

Specifically, hydroforming is executed on a tubular member on which rolling and extrusion are performed. In other words, the rear casing 512 formed by executing hydroforming on a tubular member a material of which is dense is formed to be thin, but has high airtightness. In the known cutting processing, a processing takes a long time and manufacturing cost is increased, but the rear casing 512 may be manufactured at low cost by using hydroforming.

The operating unit 57 of the camera head for an endoscope 5 according to the embodiment is attached to an outer surface of the rear casing 512 thereof using the nut Nu fixed to the outer surface of the rear casing 512 by laser welding and the screw Sc fastened to the nut Nu.

In other words, by using the nut Nu, the operating unit 57 may be attached to the rear casing 512 formed to be thin.

Other Embodiments

As described above, the embodiment for implementing the present disclosure is described, but the present disclosure is not limited to only the embodiment described above.

In the embodiment described above, an exterior unit according to the present disclosure is formed by hydroforming, but this is not limiting. The exterior unit may be formed by deep drawing processing. Even when deep drawing processing is used, the same effect as that of the embodiment is exhibited.

Figure 7:
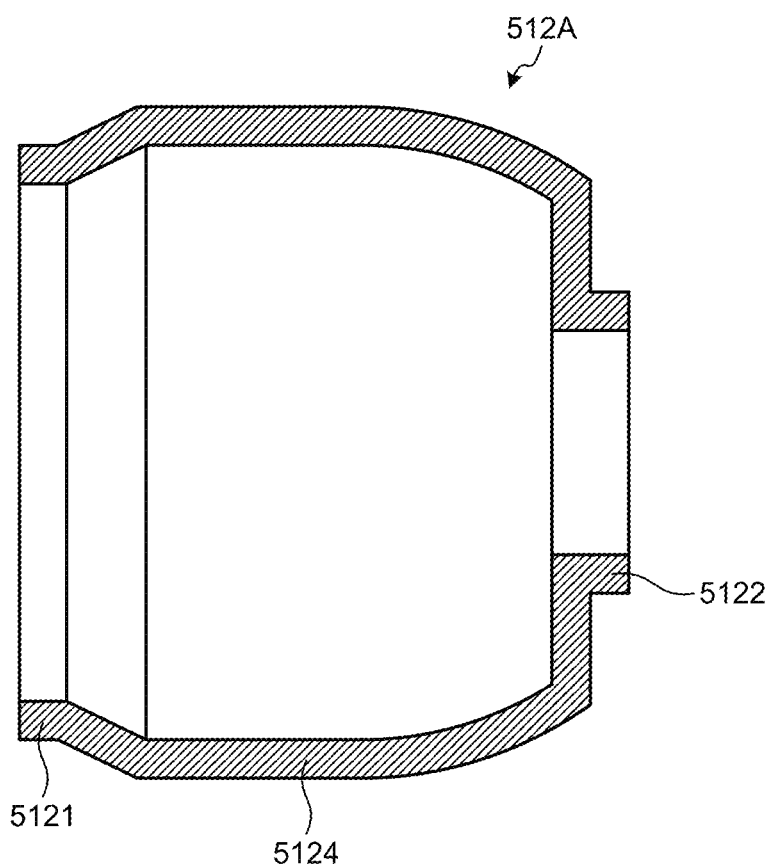
FIG. 7 is a view illustrating a modification of the embodiment.

FIG. 7 is a view illustrating a modification of the embodiment. Specifically, FIG. 7 is a sectional view illustrating a rear casing 512A according to the modification of the embodiment.

In the embodiment, the rear casing 512 extends in substantially the same internal size from the tip end part 5121 to the base end part 5122 side, and has the internal size narrowed at the base end part 5122. In other words, in the rear casing 512, the tip end part 5121 has the largest internal size. However, the exterior unit according to the present disclosure is not limited to this, and may include, using hydroforming, an intermediate part 5124 that has an internal size larger than the tip end part 5121 and the base end part 5122 between the tip end part 5121 and the base end part 5122 as illustrated in FIG. 7.

When adopted, this kind of rear casing 512A may not be formed by deep drawing processing, and, for example, makes it possible to improve the use feeling of a user such as a doctor holding the rear casing 512A by a hand.

In the embodiment, the casing 51 according to the present disclosure includes two casings that are the front casing 511 and the rear casing 512, but this is not limiting. For example, the casing 51 may be formed of one casing or three or more casings. When the casing according to the present disclosure is formed of one casing, the one casing corresponds to the exterior unit according to the present disclosure, and the one casing is formed by hydroforming or deep drawing processing.

In the embodiment, the exterior unit according to the present disclosure is formed by what is called tube hydroforming where hydroforming is executed on a tubular member, but this is not limiting. For example, the exterior unit according to the present disclosure may be formed by what is called sheet hydroforming where hydroforming is executed on a sheet member.

In the embodiment, the insertion unit 2 is not limited to a rigid endoscope and may be a flexible endoscope.

In the embodiment, the endoscopic device 1 is not limited to be used in a medical field, and may be used in an industrial field and may serve as an endoscopic device that observes the inside of a subject such as a machine structure.

In the camera head for an endoscope according to the present disclosure, the exterior unit that forms at least a part of the casing is formed by hydroforming or deep drawing processing. In other words, the exterior unit may be formed to be thin by using hydroforming or deep drawing processing. Thus, the camera head for an endoscope according to the present disclosure may achieve reduction of size and weight of an endoscopic device.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A camera head for a medical device comprising:
a casing that forms an exterior;
a sensor housed in the casing and images a subject image;
a lens housed in the casing, wherein
the casing includes a metal that forms at least a part of the exterior and surrounds the sensor, wherein the metal is a first tube with a varying internal size, the first tube being a single, inseparable tube;
an aperture at a tip end of the first tube before the lens is greater than an aperture at a base end of the first tube after the sensor, wherein an internal size and an external size of the first tube increases from the tip end and then decreases to the base end; and
an outer surface arrangement member that is fixed to an outer surface of the first tube by a screw, wherein a metal base to which the screw is fastened is connected to the outer surface of the first tube by welding.

2. The camera head for a medical device according to claim 1, wherein both ends of the first tube have respective apertures, and the first tube further includes an intermediate part between both ends thereof, the intermediate part having an internal size larger than both ends.

3. The camera head for a medical device according to claim 1, wherein the casing includes a second tube of metal, the second tube being adjacent to the first tube, and airtightly seals the casing.

4. The camera head for a medical device according to claim 3, wherein the second tube is closer to a tip end than the first tube and the second tube holds an optical element.

5. The camera head for a medical device according to claim 3, wherein an aperture of the second tube at a tip end is smaller than an aperture of the second tube at a base end.

6. The camera head for a medical device according to claim 3, wherein center axes of the first tube and the second tube coincide.

7. The camera head for a medical device according to claim 3, wherein an outer surface of the second tube that abuts the first tube is coextensive with an outer surface of the first tube.

8. The camera head for a medical device according to claim 3, wherein the second tube includes a base end that extends into the first tube and in contact with an inner surface of the first tube.

9. The camera head for a medical device according to claim 1, wherein the first tube is formed of any metal material out of aluminum, an aluminum alloy, stainless steel, titanium, and a titanium alloy.

10. The camera head for a medical device according to claim 1, further comprising a hermetic connector at a base end of the first tube.

11. The camera head for a medical device according to claim 10, wherein the base end of the first tube extends into the hermetic connector and is in contact with an outer surface of the hermetic connector.

12. The camera head for a medical device according to claim 10, wherein the first tube and the hermetic connector are connected by a weld.

13. The camera head for a medical device according to claim 1, wherein
center axes of the tip end and the base end coincide, and, further comprising, a hermetic connector at the base end that seals the casing from a transmission cable.

14. The camera head for a medical device according to claim 13, further comprising an outer shell that extends from the hermetic connector away from the first tube, the outer shell being attachably connected to the hermetic connector.

15. The camera head for a medical device according to claim 14, wherein the outer shell includes a screw groove on an outer surface.

16. The camera head for a medical device according to claim 14, further comprising a base end seal that seals the hermetic connector, the transmission cable, and the first tube, the base end seal being attachably connected to the outer shell.

17. A camera head for a medical device comprising:
a casing that forms an exterior;
a sensor housed in the casing and images a subject image;
a lens housed in the casing, wherein
the casing includes a first tube that forms at least a part of the exterior and surrounds the sensor, wherein the first tube has a varying internal size;
an aperture at a tip end of the first tube before the lens is greater than an aperture at a base end of the first tube after the sensor;

a hermetic connector at the base end that seals the casing from a transmission cable; and an outer shell that extends from the hermetic connector away from the first tube, the outer shell being attachably connected to the hermetic connector, the outer shell including a screw groove on an outer surface.

18. The camera head for a medical device according to claim 17, further comprising a base end seal that seals the hermetic connector, the transmission cable, and the first tube, the base end seal being attachably connected to the outer shell, the base end seal including a screw groove on an inner surface thereof that corresponds to the screw groove on the outer surface of the outer shell.

19. The camera head for a medical device according to claim 17, wherein the first tube is metal.

20. The camera head for a medical device according to claim 17, wherein the first tube is a single, integral tube.

21. The camera head for a medical device according to claim 17, wherein the center axes of the tip end and the base end coincide.

22. A camera head for a medical device comprising:
a casing that forms an exterior;
a sensor housed in the casing and images a subject image;
a lens housed in the casing, wherein
the casing includes a first tube that forms at least a part of the exterior and surrounds the sensor, wherein the first tube has a varying internal size;
an aperture at a tip end of the first tube before the lens is greater than an aperture at a base end of the first tube after the sensor;
a hermetic connector at the base end that seals the casing from a transmission cable;
an outer shell that extends from the hermetic connector away from the first tube; and
a base end seal that seals the hermetic connector, the transmission cable, and the first tube, the base end being attachably connected to the outer shell.

23. The camera head for a medical device according to claim 22, wherein the base end seal includes a cable bushing and a seal between the cable bushing, the hermetic connector and the first tube.

24. The camera head for a medical device according to claim 22, wherein the first tube is metal.

25. The camera head for a medical device according to claim 22, wherein the first tube is a single, integral tube.

26. The camera head for a medical device according to claim 22, wherein the center axes of the tip end and the base end coincide.

27. A camera head for a medical device, comprising:
a casing that forms an exterior;
a sensor housed in the casing and images a subject image;
a lens housed in the casing, wherein
the casing includes a metal that forms at least a part of the exterior and surrounds the sensor, wherein the metal is a first tube with a varying internal size;
an aperture at a tip end of the first tube before the lens is greater than an aperture at a base end of the first tube after the sensor;
an outer surface arrangement member that is fixed to an outer surface of the first tube by a screw, the outer surface arrangement member including an operational button and an insertion hole for the screw; and
a metal base to which the screw is fastened is connected to the outer surface of the first tube, wherein a portion of the metal base beneath the insertion hole extends into the outer surface of the first tube such that portion of the metal base is between an end of the screw and the outer surface of the first tube.

* * * * *